United States Patent [19]

Fischer

[11] 3,955,926

[45] May 11, 1976

[54] PROCESS AND QUICK-ACTION REAGENT FOR THE DETECTION OF NARCOTICS

[75] Inventor: Wolfgang Fischer, Darmstadt, Germany

[73] Assignee: Merck Patent Gesellschaft mit beschrankter Haftung, Darmstadt, Germany

[22] Filed: Feb. 12, 1973

[21] Appl. No.: 331,596

[30] Foreign Application Priority Data

Feb. 12, 1972   Germany............................ 2206697

[52] U.S. Cl. ........................ 23/230 B; 23/253 TP; 252/408
[51] Int. Cl.² .................. G01N 21/06; G01N 33/16
[58] Field of Search ............ 23/230 B, 253 TP, 292; 252/408

[56] References Cited
UNITED STATES PATENTS

| | | | |
|---|---|---|---|
| 1,975,245 | 10/1934 | Zackheim ............................ | 23/292 |
| 2,986,453 | 5/1961 | Collins ............................ | 23/253 TP |
| 3,146,070 | 8/1964 | Collins ............................ | 23/253 TP |
| 3,378,346 | 4/1968 | Watson ............................ | 23/253 TP |
| 3,447,904 | 6/1969 | Rupe ............................ | 23/253 TP |
| 3,453,180 | 7/1969 | Fraser ............................ | 23/253 TP |
| 3,526,479 | 9/1970 | Rey ............................ | 23/253 TP |
| 3,656,906 | 4/1972 | Bullock ............................ | 23/230 B |
| 3,761,227 | 9/1973 | Conrad ............................ | 23/230 B |
| 3,832,134 | 8/1974 | Sohn ............................ | 23/253 TP |

OTHER PUBLICATIONS

J. Look, J. Pharm. Sci., 56 (11), 1526–1527 (1967).
Chemical Abstracts, 56: 1529b (1962).

*Primary Examiner*—Morris O. Wolk
*Assistant Examiner*—Sidney Marantz
*Attorney, Agent, or Firm*—Millen, Raptes & White

[57] ABSTRACT

A quick-action reagent for the detection of narcotics comprising a solvent for the narcotic and a color reagent, at least one component of which is impregnated in an absorbent substrate.

3 Claims, 4 Drawing Figures

U.S. Patent May 11, 1976 3,955,926
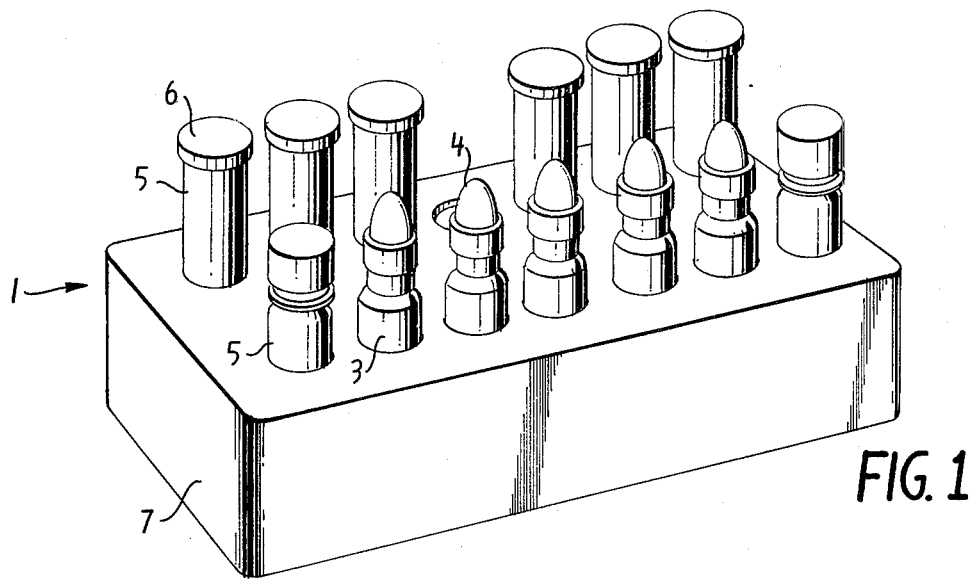
FIG. 1
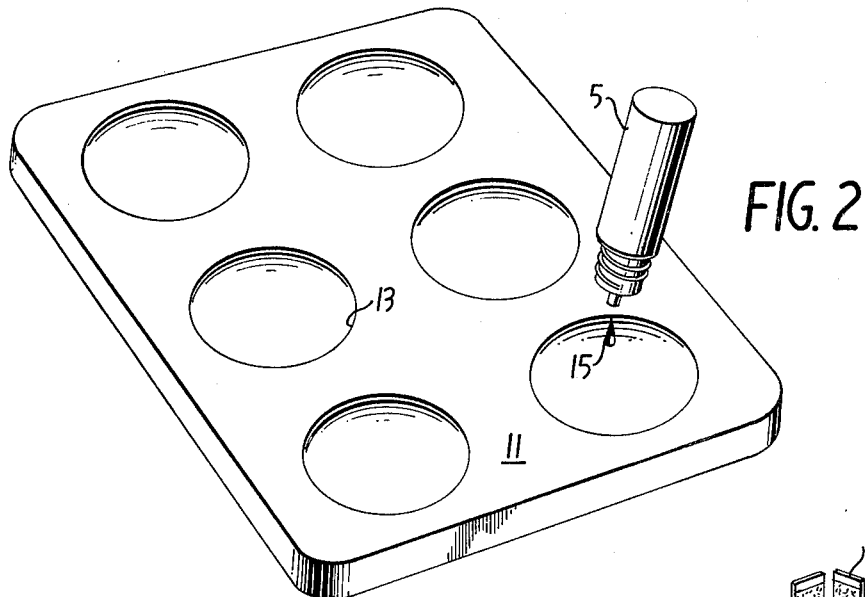
FIG. 2
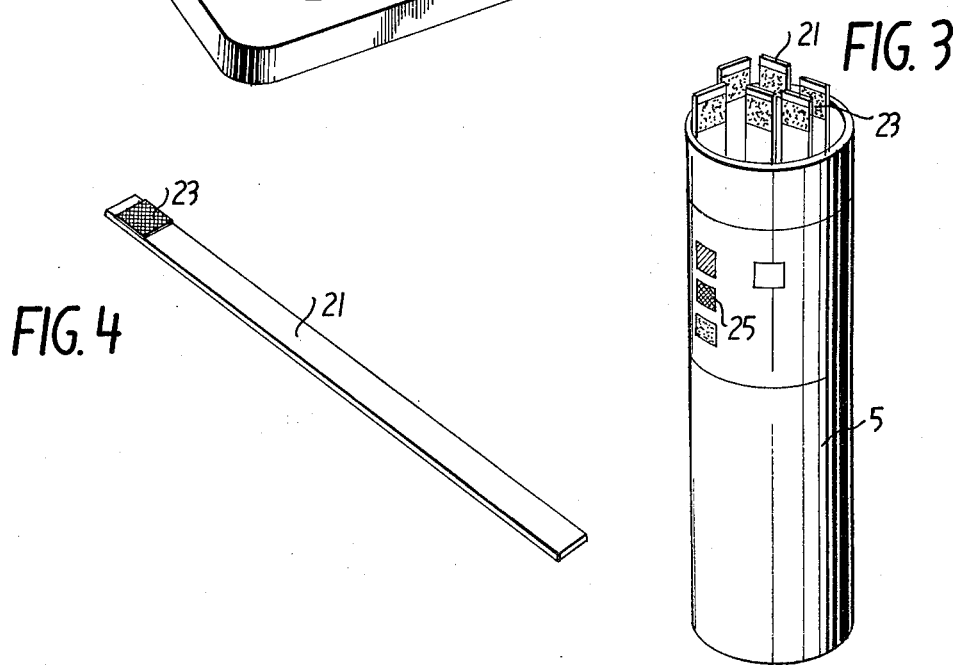
FIG. 3
FIG. 4

PROCESS AND QUICK-ACTION REAGENT FOR THE DETECTION OF NARCOTICS

BACKGROUND OF THE INVENTION

From year to year, there is an increase in the alarming news of the rising abuse of substances with narcotic effects, e.g., hashish, opium, morphine, morphine derivatives, heroin, cocaine, lysergic acid diethylamide (LSD), and so forth. Experts in this field have no appreciable difficulty in detecting narcotics in a well-equipped laboratory, since gas and thin-layer chromatography, ultraviolet, infrared, nuclear resonance, and mass spectrometry permit an exact characterization and identification of the individual narcotics. However, such an array of instruments is expensive and cumbersome, since the time consumed for the investigations is considerable. Consequently, there is a need for a rapid and reliable test which will prermit the government agencies involved in combating the trading in and consumption of narcotics to qualitatively indentify the most common narcotics outside of the laboratory.

Reagents for the detection of various narcotics are known in the literature. For example, see Arch. Toxikol. 25, 19 (1969), J. Pharm. Sci. 56, 1526 (1967). The most frequently employed determination methods involve color reactions which are more or less specific to certain narcotics. The conventional analytical use of color reactions comprises the preparation of the required reagents and other procedures relating to laboratory technique and apparatus which, in addition to being time-consuming, are difficult and therefore must be executed by experienced personnel. Thus, the use of these conventional procedures for the identification of substances suspected of being narcotics at the immediate location is unsuitable for an amateur. Additionally, the conventional ready-for-use reagents have only a very limited stability.

It has now been found that these disadvantages can be avoided by using, for the detection of the most common narcotics, the detection method and product of this invention.

SUMMARY OF THE INVENTION

The narcotics detection method of this invention employs a quick-action reagent comprising a solvent for the narcotic and an absorbent support containing at least one component of the color reagent in dry form. In this manner, the stability of ready-to-use reagent solutions for the detection of narcotics is ensured. Shelf-stable quick-action reagents are obtained, by means of which narcotics can be rapidly and safely identified qualitatively by comparison with a color scale.

Thus, in its process aspect, this invention relates to a rapid process for the detection of narcotics by dissolution of a sample of the suspected narcotic in a solvent for the sample and reaction of the solution with a color reagent, at least one component of which is employed in dry form on an absorbent support.

In its product aspect, this invention comprises a quick-action reagent for the detection of narcotics, comprising a solvent for the narcotic and a color reagent, at least one component of the color reagent being in dry form adsorbed on an absorbent support.

DETAILED DISCUSSION

Optionally, one or more components of a multi-component color reagent can be dissolved in the solvent employed in the process of this invention, to dissolve the narcotics prior to the actual indicating reaction, so long as at least one component of the color reagent is employed in dry form adsorbed on an absorbent support. For example, a quick-action reagent according to the present invention for the detection of cocaine contains ammonium thiocyanate as a dry component of the color reagent on an absorbent support and cobalt (II) chloride as a further component dissolved in the solvent employed (acetic acid).

The quick-action reagent according to this invention and process employing it are suitable in general for the detection of all narcotics, particulaly the following: hashish, opium, morphine, morphine derivatives, heroin, cocaine, lysergic acid diethylamide (LSD), amphetamine, benzedrine, mescaline and barbiturates. As a further indication of the versality of the process of this invention, the entire group of alkaloids can be detected, which includes almost all common narcotics. For example, of the aforementioned narcotics, only the active agents in hashish are not alkaloids.

The process is conducted employing reactions known per se for the detection of narcotics. However, in the process or quick-action reagent of the present invention, at least one component of the color reagent employed is provided in dry form adsorbed on an absorbent support. Suitable absorbent supports include all those which are customarily utilized for such indicator reagents. Although filter paper is the most commonly used, it is also possible to employ other absorbent cellulose or synthetic resin products and fiber-glass paper. The impregnated papers can either be cut, as such, into convenient strips, or they can be processed into preferably square sections which, in turn, can be conventionally glued or sealed onto or into synthetic resin sheets, paper strips, or metal strips.

DESCRIPTION OF THE DRAWINGS

With reference to the drawings:

FIG. 1 is a perspective view of a kit according to this invention showing a plurality of stoppered bottles, some of which have eye-dropper caps, and a plurality of containers with lids, all fitted into a tray-like holder;

FIG. 2 is a perspective view of an optional spot-testing plate into which a drop is shown being transferred from a bottle;

FIG. 3 is a detailed perspective view of a container with its top removed showing protruding therefrom the ends of a plurality of paper strips having a portion impregnated; and FIG. 4 is a perspective view of a paper strip shown in FIG. 3, showing the area thereon impregnated.

In the preferred embodiment shown in the drawings, a test kit 1 for narcotic detection according to this invention consists of a spottesting plate, i.e., a porcelain plate 11 with cup-shaped indentations 13, and a tray 7 into which is fitted, for each of the above-described narcotics, a bottle 3 with cap 4 containing a solvent for that narcotic and an associated vial 5 with cap 6 containing an indicator strip 21 having an end portion 23 impregnated with at least one component of the color indicator for that narcotic, a blank strip, and a color comparison scale 25. On the color scale, in addition to a negative color value, several positive color values are provided, since the color intensity obtained depends on the concentration of the existing narcotic in the unknown being tested. Optionally, a spatula is provided for depositing a determined amount of the unknown on-the-spot testing plate.

The quick-action reagent for conducting a narcotic indication according to this invention consists respectively of a specific solvent and an associated indicator strip (stick). The detection is preferably conducted by first introducing, using a small spatula, a sample of the material to be investigated for narcotic content into an indentation 13 of a spot-testing plate 11. Then, 1–10 droplets 15 of a solvent for a specific narcotic are added thereto. After a few minutes, the impregnated portion 23 of the corresponding indicator strip 21 is briefly immersed into the solvent solution and any coloration which develops on the indicator strip is compared with the associated color comparison scale.

The test process of this invention is especially suitable for the identification of narcotics in solid form. Difficulties may arise in the examination of dilute solutions or strongly colored substances, especially if the color of the reaction is masked by the inherent color of the material to be investigated. However, this disadvantage has a much greater effect in the conventional detection reactions, due to the large layer thickness of the solution in the test tube, than in case of using the indicator strips. Thus, for example, the detection of morphine in opium is not too simple, because the opium has a morphine content of only about 10% and also the color indication is made difficult by the inherent brownish color of opium. In this case, a blank strip, i.e., a strip without any reagent in the reaction zone, is dipped into the solution to be tested, and the thus-produced color is compared with the color on the actual indicator strip. The blank strip, in case of strongly colored solutions, constitutes the color value for a negative reaction.

To produce the test kits of this invention, the selected support, preferably filter paper, is uniformly impregnated with a component of a color reagent for a selected narcotic to provide a concentration of the component in the support effective to effect the desired color change when the impregnated carrier is contacted with a solution of the appropriate narcotic. The absorbent carrier is usually impregnated in a conventional manner so as to provide a pickup of the solution of about 100–700%, preferably about 150–300%, calculated on the dry weight of the carrier. The impregnated carrier is then air or preferably oven dried. The dried carrier can then either be cut into handy strips, or they can be processed into preferably square pieces, which can then be conventionally glued onto plastic films, paper strips, or metallic strips, or sealed onto or into such films and strips.

The indicators of this invention, as they are used for the detection of narcotics, comprise a dry absorbent carrier uniformly impregnated (per $m^2$ of surface area) with 1–100 g., preferably 5–50 g., of a component of a color reagent for a narcotic, in combination with a solvent for the narcotic which, with the component impregnated in the adsorbent carrier, contains the remaining portion of the color reagent for the narcotic for which the reagent is a detector. In the table hereinafter is given an illustrative peferred distribution of multi-component reagents for the most common narcotics.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

DETECTION OF HASHISH

The resin of the flowering tops of Indian hemp (Cannabis sativa var. indica) is known under the Arabian designation of "hashis". The Mexican name "marihuana" denotes cut leaves and flowers of Indian hemp. The resin, in most cases, is smoked in a mixture with tobacco. In addition to cannabol, cannabidiol, or cannabidiol-carboxylic acid, isomeric tetrahydrocannabinols are considered as the primary hallucinogenically active agents. The detection of hashish is based on the red coloring produced by "Echtblausalz B" (tetraazotized di-o-anisidine $C_{14}H_{12}Cl_2N_4O_2$) in an alkaline medium in the presence of such agents.

The quick-action reagent of this invention for the detection of hashish consists of an aqueous-alcoholic alkaline solution as the solvent and an absorbent support impregnated with Echtblausalz B, zinc chloride and, optionally, fluoboric acid.

The solvent consists preferably on 1N aqueous sodium hydroxide solution in ethanol in a ratio of about 1 : 2. The impregnating solution for the absorbent support preferably contains 0.1–2% Echtblausalz B, 1–10% zinc chloride, and optionally 0–1% 35% strength fluoboric acid in methanol/water (3 : 2).

DETECTION OF OPIUM

Opium is the air-dried milky juice which exudes when unripe capsules of the poppy (Papaver somniferum) are cut. Addictive drugs contained in opium are, inter alia, morphine, codeine, as well as thebaine, which are bound to meconic acid. The detection of opium is based on the reaction of iron(III) salts with meconic acid.

The quick-action reagent of this invention for the indication of opium consists of a dilute acid as the solvent and an absorbent support impregnated with ammonium iron(III) sulfate.

The solvent is preferably dilute acetic acid. The impregnating solution for the absorbent support preferably contains 1–20% of ammonium iron(III) sulfate in water.

DETECTION OF MORPHINE

Morphine is the most important opium alkaloid. The morphine content in opium is about 10%. Morphine is still produced from opium, because the total synthesis of this substance is uneconomical. The morphine detection is based on the violet coloring produced by oxidized morphine with iron(III) salts in an alkaline medium.

The quick-action reagent of this invention for the detection of morphine consists of iodic acid in a dilute acid as the solvent, and of an absorbent support impregnated with iron(III) chloride, alkali tartrate, and alkali carbonate.

The solvent consists preferably of 0.01–5% strength iodic acid in dilute acetic acid. The impregnating solution for the absorbent support preferably contains 0.1–1% of iron(III) chloride, 1–10% of sodium tartrate, and 1–20% of sodium carbonate in water.

DETECTION OF MORPHINE DERIVATIVES

The derivatives of morphine exhibit similar effects as morphine itself. These derivatives are likewise commercially available as drugs. The best-known morphine derivative is codine, the methyl ether or morphine. Further known drugs are, for example, the morphine derivatives ethylmorphine, dihydrocodeinone, dihydromorphinone, dihydroxycodeinone, dihydrocodeinone enol acetate, and dihydrocodeine. By reaction of the morphine derivatives with sulfuric acid, apomorphine is obtained. The actual indication is based on the color reaction of apomorphine with formaldehyde.

The quick-action reagent of this invention for the indication of morphine derivatives consists of sulfuric acid as the solvent and an absorbent support impregnated with hexamethylenetetramine.

The solvent consists preferably of 65–95% strength sulfuric acid. The impregnating solution for the absorbent support contains peferably 1–20% of hexamethylenetetramine in methanol/water (3 : 1).

DETECTION OF HEROIN

Heroin, a diacetylmorphine, is an especially strong narcotic and therefore leads very rapidly to addiction. It is detected by first splitting off the acetyl groups and then color detecting the thus-formed morphine, as described above.

The quick-action reagent for the detection of heroin is characterized in that the solvents employed are first benzylamine and then a dilute acid containing iodic acid. The absorbent support is impregnated with iron-(III) chloride, alkali tartrate, and alkali carbonate.

The dilute acid containing iodic acid, as used as the solvent, consists preferably of 0.01–5% stength iodic acid in dilute hydrochloric acid. The impregnating solution for the absorbent support contains preferably 0.1–1% of iron(III) chloride, 1–10% of sodium tartrate, and 1–20% of sodium carbonate in water.

DETECTION OF COCAINE

Cocaine occurs in the leaves of the coca bush (Erythroxylon coca) and is the methyl ester of benzoylecgonine. Due to the high danger of addiction and the toxicity, cocaine abuse is even more destructive in its consequences than the consumption of morphine. Cocaine is sniffed in most cases, because it is particularly well resorbed by the mucous membranes. The detection is based on the indicaion that the pink color of a solution of cobalt(II) thiocyanate changes to blue in the presence of cocaine.

The quick-action reagent of this invention for the detection of cocaine consists of a dilute acid containing a cobalt(II) salt, as the solvent, and an absorbent support impregnated with ammonium thiocyanate.

The solvent consists preferably of approximately 6% strength acetic acid containing dissolved therein about 2.5% of cobalt(II) chloride. The impregnating solution for the absorbent support preferably contains 1–20% of ammonium thiocyanate in methanol.

DETECTION OF LYSERGIC ACID DIETHYLAMIDE (LSD)

Probably the best known and most widespread hallucinogen is lysergic acid diethylamide, obtainable by the semisynthetic modification of the ergot alkaloid ergobasine. The detection of LSD is based on the violet-blue color reaction with p-dimethylaminobenzaldehyde. Other indole members, such as, for example, dimethyltryptamine, diethyltryptamine, bufotenine, serotonin, and psilocybin also produce a color reaction which is more violet-red.

The quick-action reagent of this invention for the detection of LSD consists of mineral acid as the solvent and an absorbent support impregnated with p-dimethylaminobenzaldehyde, polyvinylpyrrolidone, and optionally oxalic acid.

The solvent consists preferably of 10–90% strength hydrochloric acid. The impregnating solution for the absorbent support contains preferably 1–30% of p-dimethylaminobenzaldehyde, 0.5–4% of polyvinylpyrrolidone, and 0–15% of oxalic acid in methanol.

DETECTION OF ALKALOIDS

Since the narcotics involve almost exclusively alkaloids, it is advantageous to first detect an entire group of narcotics by a general alkaloid indication step, before conducting a specific test in connection with a certain narcotic. This indication procedure is based on the color reaction with Dragendorff reagent.

The quick-action reagent of this invention for the detection of alkaloids consists of a dilute acid as the solvent and an absorbent support impregnated with basic bismuth nitrate, tartaric acid, and potassium iodide.

The solvent preferably consists of dilute acetic acid. The impregnating solution for the absorbent support contains preferably 0.5–5% of basic bismuth nitrate, 5–25% of tartaric acid, and 5–30% of potassium iodide in water.

DETECTION OF AMPHETAMINE AND MESCALINE

The quick-action reagent of this invention for the detection of amphetamine and mescaline consists of sulfuric acid as the solvent and an absorbent support impregnated with hexamethylenetetramine and etylene glycol.

The solvent consists preferably of 70–100% strength sulfuric acid. The impregnating solution for the absorbent support preferably contains 3–20% of hexamethylenetetramine and 0–5% of ethylene glycol in methanol/water (3 : 1).

DETECTION OF BARBITURATES

The quick-action reagent of this invention for the detection of barbiturates consists of pyridine containing a cobalt(II) salt, as the solvent, and an absorbent support impregnated with an alkali hydroxide.

The solvent consists preferably of a 0.1–1.0% strength solution of cobalt(II) chloride in pyridine. The impregnating solution for the absorbent support contains preferably 5–30% of lithium hydroxide in water.

EXAMPLE

Several milligrams or a few droplets of the unknown material to be tested are introduced into the indentation of a spot-testing plate. Then 1–10 droplets of a solvent (Column 2) are added thereto, and the sample is dissolved by agitation, or the narcotic is segregated by this dissolving step. Thereafter, the indicator strip, impregnated with a component of the color detection reagent corresponding to the solvent employed, is immersed until the zone of the reagent impregnated in the indicator step is fully wetted, and the thus-produced possible color change (Column 5) is compared with the appropriate color comparison scale.

If the indication is negative, the procedure is repeated with another solvent and the respectively associated impregnated indicator strips.

In this detection kit and process, the indicator strip employed was impregnated with a solution containing 0.5% iron(III) chloride, 2.5% sodium tartrate and 15% sodium carbonate in water. Five milligrams of a heroin suspicious material were introduced into the indentation of a spot-testing plate. Firstly one droplet of benzylamine is added thereto and stirred. After a minute ten droplets of 0.1% iodic acid in 1N hydrochloric acid are added and the containing heroin is dissolved by agitation. Thereafter, the indicator strip is immersed, whereby color changed from colorless to light brown, this color corresponds to approximately 20 γ on the color comparison scale.

contacting the solution with a multi-component color reagent for the narcotic, the improvement wherein (a) samples of the unknown are separately tested for heroin and for morphine derivatives with a multi-component reagent for heroin and a multi-component reagent for morphine derivatives, (b) at least one component of each of said reagents is in dry form impregnated in an absorbent support and the remaining component thereof is in liquid form, (c) the component of the reagent for heroin in liquid form is a solution of benzylamine and iodic acid in dilute acid and the dry component thereof is an absorbent support impregnated with ferric chloride, an alkali tartrate and an alkali carbonate, and (d) the liquid component for morphine derivatives is sulfuric acid and the dry component thereof is an absorbent support impregnated with hexamethylenetetramine.

TABLE

| 1 NARCOTIC | 2 SOLVENT | 3 IMPREGNATING SOLUTION | 4 DETECTION LIMIT | 5 COLOR CHANGE |
|---|---|---|---|---|
| Hashish | 1N NaOH/ ethanol 1 : 2 | 0.6% Tetraazotized di-o-anisidine 3.2% Zinc chloride 0.1% Fluoboric acid (35%) in $CH_3OH/H_2O$ 3:2 | 5γ | red — colorless |
| Opium | 0.5% Acetic acid | 5% Ammonium iron(III) sulfate in water | 10γ | brown — colorless |
| Morphine | 0.7% Iodic acid in 1% acetic acid | 0.5% Iron(III) chloride 2.5% Sodium tartrate 15% Sodium carbonate in water | 10γ | violet — colorless |
| Morphine derivatives | 80% Sulfuric acid | 10% Hexamethylenetetramine in methanol/water 3 : 1 | Morphine 10γ Heroin 10γ | violet — colorless |
| Heroin | Benzylamine 0.1% iodic acid in 1N HCl | 0.5% Iron(III) chloride 2.5% Sodium tartrate 15% Sodium carbonate in water | 10γ | brown — colorless |
| Cocaine | 2.5% $CoCl_2$ in 6% acetic acid | 6% Ammonium thiocyanate in methanol | 20γ | blue — pink |
| Lysergic acid diethyl-amide (LSD) | 25% Hydrochloric acid | 15% p-Dimethylaminobenzaldehyde 2% Polyvinylpyrrolidone 10% Oxalic acid in methanol | 0.5γ | violet — colorless |
| Alkaloids | 0.1N Acetic acid | 1% Basic bismuth nitrate 13% Tartaric acid 20% Potassium iodide in water | 10γ | orange — yellow |
| Amphetamine Mescaline | 96% $H_2SO_4$ | 10% Hexamethylenetetramine 2% Ethylene glycol in $CH_3OH/H_2O$ 3 : 1 | 5γ | reddish brown — colorless |
| Barbiturates | 0.7% $CoCl_2$ in pyridine | 20% Lithium hydroxide in water | 10γ | blue/yellowish violet — colorless |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the detection of narcotics by dissolution of the unknown in a solvent for the narcotic and 2. A process according to claim 1 wherein the component of the reagent for heroin in liquid form is a solution of benzylamine and 0.1% iodic acid and 1 N HCl and the dry component is paper impregnated with a solution of about 0.5% ferric chloride, about 2.5% sodium tartrate and 15% sodium carbonate in water and then dried.

3. A process according to claim 1 wherein the component of the reagent for morphine derivatives in liquid form is 65–95% sulfuric acid and the absorbent for the component thereof in dry form is paper.

* * * * *